United States Patent [19]

Rudolph

[11] Patent Number: 5,060,655
[45] Date of Patent: Oct. 29, 1991

[54] PNEUMOTACH

[75] Inventor: Kevin A. Rudolph, Kansas City, Mo.

[73] Assignee: Hans Rudolph, Inc., Kansas City, Mo.

[21] Appl. No.: 271,607

[22] Filed: Nov. 15, 1988

[51] Int. Cl.$^5$ .............................................. A61B 5/08
[52] U.S. Cl. ..................................... 128/716; 128/725
[58] Field of Search ............................... 128/716, 725; 73/861.52, 3

[56] References Cited

U.S. PATENT DOCUMENTS

| | | | |
|---|---|---|---|
| 3,504,542 | 4/1970 | Blevins | 73/861.52 |
| 3,626,755 | 12/1971 | Rudolph | 73/861.52 |
| 4,384,469 | 5/1983 | Murphy | 73/3 |
| 4,403,514 | 9/1983 | Osborn | 128/725 |

*Primary Examiner*—Edgar S. Burr
*Assistant Examiner*—Aaron J. Lewis
*Attorney, Agent, or Firm*—Litman, McMahon & Brown

[57] ABSTRACT

A pneumotach apparatus for measuring gas flows comprises a flow head with a passageway and having a plurality of screens positioned in the pasageway to provide a variance in pressure on different sides of one of the screens, a pressure transducer to convert the pressures into a flow value and a display or recorder for conveying the pressure readings to an operator. The apparatus includes improved seals between the screens, improved seals between pressure taps and the screens, improved sealing between a mounting plate for the taps and a housing for the screens, and knife edges on tube adaptors for the housing that are positioned in close proximity to the screens to improve the accuracy of flow measurements taken by the apparatus.

7 Claims, 2 Drawing Sheets

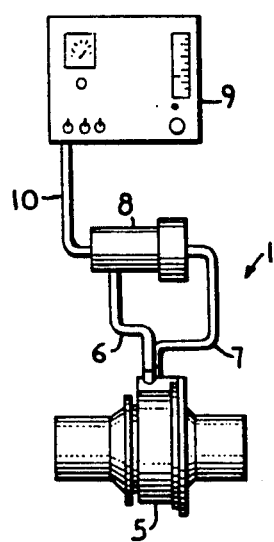
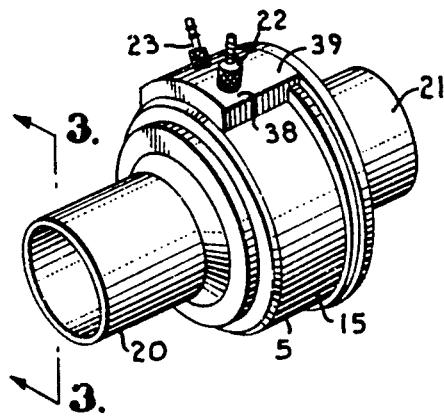
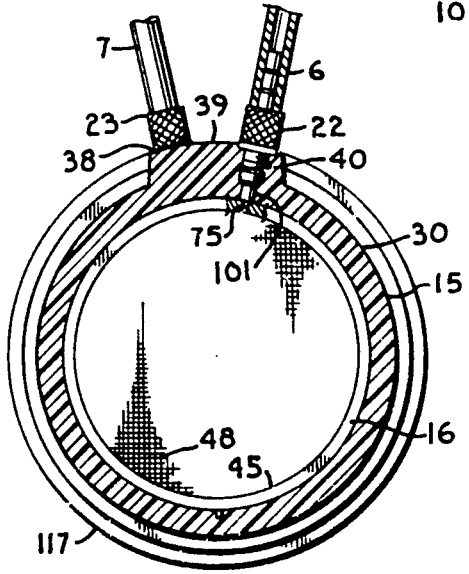
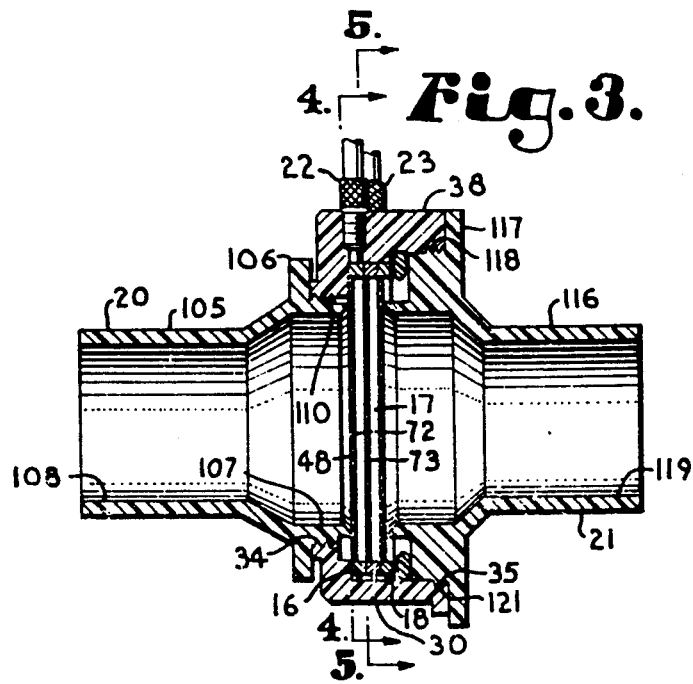
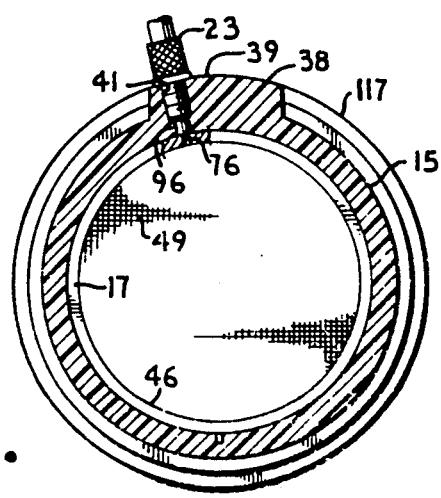

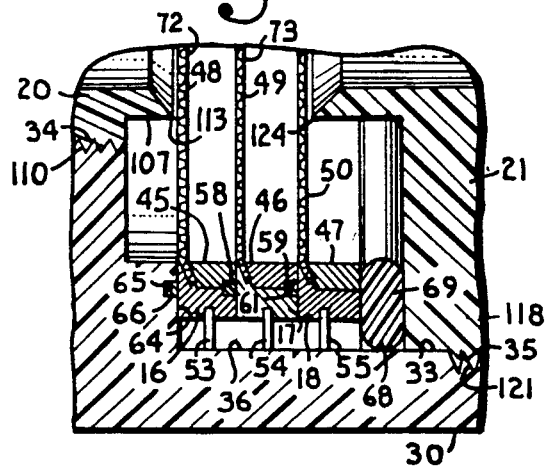
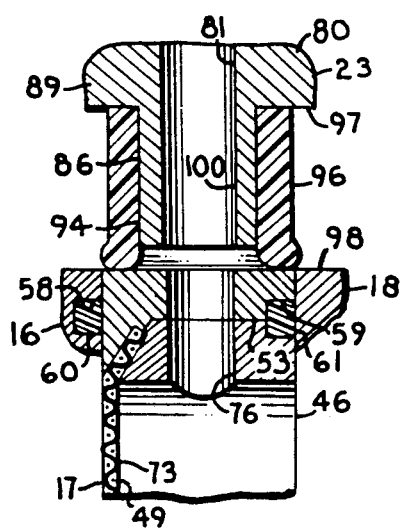
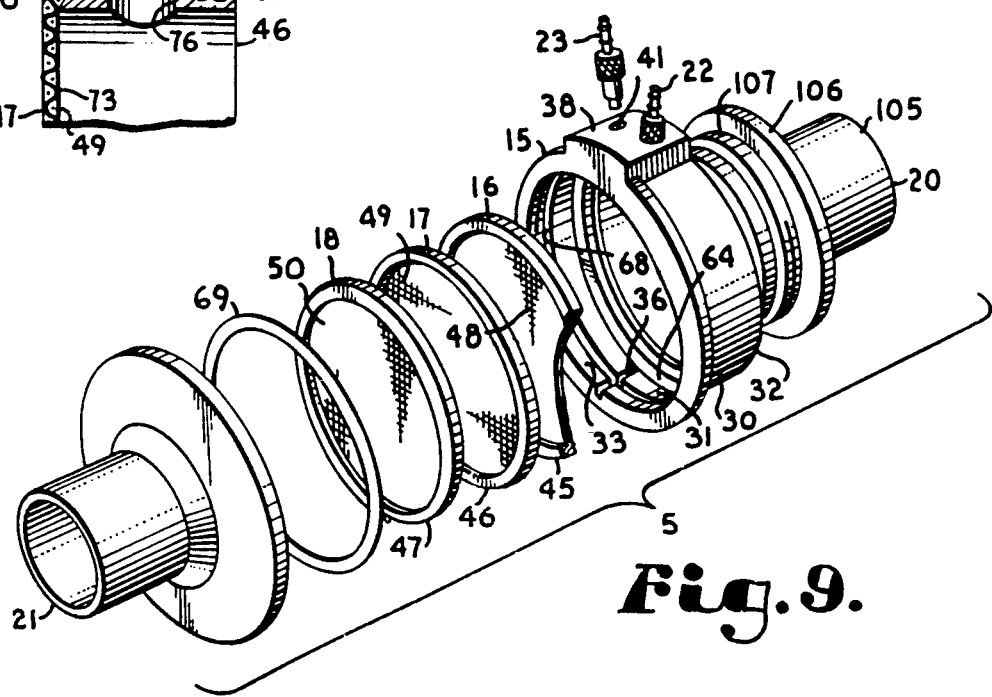

PNEUMOTACH

BACKGROUND OF THE INVENTION

The present invention relates to apparatus for measuring fluid flow and, in particular, to an apparatus for the measurement of respiratory gases that are inhaled and exhaled from a human or other animal. Pneumotach apparatus of the type described herein include a pheumotachometer which is the flow measuring head and pneumotachographs which comprise equipment used in conjunction with the flow heads to provide a visual or recorded flow measurement to an operator.

Various types of pneumotach apparatus have been used for a number of years, especially in the measurement of respiratory gases so as to provide scientists, doctors, exercise physiologists and the like with a relatively accurate flow measurement of a person or animal undergoing various pulmonary physiological tests including physical exercise or stress inducing activities to determine the effect of such activities on the quantity of air or the like breathed by the person or animal. Such apparatus is also used in measuring resuscitator flows to patients during surgery, comas or related medical events where mechanically assisted breathing is required. For some tests, the exhaled gases are also analyzed to determine the component parts thereof and to allow a physician, scientist or other operator to better determine the metabolism and breathing capabilities of the party being tested.

For certain types of tests the need for improved accuracy in gas flow measurement is steadily increasing. Whereas at one time only a general or relative flow rate was required from devices designed and sized for a typical adult range of individuals, now tests have been devised to broaden that range to include, for example, children and animals and the accuracy of the flow measurements required has substantially increased.

A conventional pneumotach apparatus is shown in U.S. Pat. No. 3,626,755 of H. Rudolph which is incorporated herein by reference. Although the apparatus illustrated in the original Rudolph patent was quite satisfactory for the requirements of the industry for that period of time, as mentioned above, modern requirements are for a substantially improved measurement capability.

In particular, in the original device O-rings were usually utilized at the base of pressure sensing taps to seal these taps against annular rings supporting screens used therein. Unfortunately, because the annular rings have a curved surface and the taps have a planar surface nearest the annular rings, it was quite difficult for the O-rings to seat correctly and there was usually some leakage thereabout. Even a fairly minor leakage of this type can effect the measurement capability.

Secondly, in the original pneumotachs, it was possible for gas flows to flow between and around the outer annular surface of the screen support rings so as to by-pass the screens. Depending upon where this by-pass occurs, the resultant measurement varies and is inaccurate.

Thirdly, in the original pneumotach devices the plate for supporting the taps was independent from the remaining part of the outer housing for the device. This allowed leakage between the innerconnection of the parts.

Finally, it has been found that the tubular delivery of gases to and from the screens in an uncontrolled manner produces turbulence and other problems that effect flow measurement. In particular, the relatively flat ends of the tubes aligned parallel to the screens and the substantial spacing of these ends from the screens have been found to create turbulent flow and other problems in the vicinity of the screens, thereby effecting flow measurement.

OBJECTS OF THE INVENTION

Therefore, the objects of the present invention are: to provide an improved pneumotach apparatus for measuring respiratory gas flows and the like; to provide such an apparatus having a main housing, first and second respiratory gas tubing adaptors connected to the main housing, a plurality of screens within the main housing and aligned normal to the passgeway and a pair of taps for transferring gas pressure on opposite sides of at least one of the screens to a transducer for converting gas pressures from the taps into a gas flow output for visual display or recording for use by the operator; to provide such an apparatus having improved sealing between the taps and the spaces on either sides of at least one of the screens and, in particular, to a sealing sleeve that allows a high degree of sealing between the taps and flow connecting bores in annular rings associated with the screens; to provide such an apparatus having sealing means between the annular rings associated with each of the screens so as to reduce gaseous by-pass around the screens; to provide such an apparatus having a mounting plate that is integral with the housing and for supporting the taps, so as to prevent leakage between the plate and the housing; to provide such an apparatus having inlet and outlet tubing configured to reduce turbulence and improve accuracy of output data of the apparatus; to provide such an apparatus wherein both the inlet and outlet tubings end in knife edges which are closely spaced relative to screens on opposite sides of the apparatus main housing so as to improve accuracy of the output data of the apparatus; and to provide such an apparatus which is relatively easy to manufacture, simple to use, highly accurate in providing flow readings and especially well-adapted for the intended usages thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a side elevational view of a pneumotach apparatus, including a pneumotach flow head, in accordance with the present invention.

FIG. 2 is an enlarged and perspective view of the flow head.

FIG. 3 is an enlarged and cross-sectional view of the flow head, taken along line 3—3 of FIG. 2.

FIG. 4 is an enlarged and cross-sectional view of the flow head, taken along line 4—4 of FIG. 3.

FIG. 5 is an enlarged and cross-sectional view of the flow head, taken along line 5—5 of FIG. 3.

FIG. 6 is a further enlarged, fragmentary and cross-sectional view of the flow head, similar to FIG. 3.

FIG. 7 is a further enlarged, fragmentary and cross-sectional view of the flow head of a portion of the flow head, as shown in FIG. 3.

FIG. 8 is a still further enlarged, fragmentary and cross-sectional view of the flow head, taken along line 8—8 of FIG. 7.

FIG. 9 is an enlarged and exploded perspective view of the flow head, with portions thereof broken away to illustrate detail.

DETAILED DESCRIPTION OF THE ILLUSTRATED EMBODIMENT

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally indicates a pneumotach apparatus in accordance with the present invention. The pneumotach apparatus 1 comprises a flow measuring head 5 flow connected by a pair of flexible tubes 6 and 7 to a pressure transducer 8 which is in turn connected to a flow indicating instrument 9 by a conduit 10.

The pressure transducer 8 is of a conventional type adapted to sense a differential pressure between the interiors of tubes 6 and 7 and converts the differential pressure into a flow measurement of the gas passing through the flow measuring head 5, as will be described below. The flow measurement is conducted by the conduit 10 to a conventional flow indicating instrument 9 which may provide a read-out to an operator thereof of the type that can be visually determined and/or permanently recorded or may be virtually any instrument which provides the operator with the ability to determine the flow in the head 5 based upon a differential pressure drop across a restrictive screen or related device. The calculations necessary to convert the pressure differential across a restrictive screen into a flow measurement are well known in the art.

The flow head, which can be seen in an exploded view in FIG. 9, comprises a housing 15, three foraminous members such as screen members 16, 17 and 18, a first tube adaptor 20, a second tube adaptor 21, a first tap 22 and a second tap 23.

The housing 15 comprises a generally annular ring 30 having an interior passageway 31 passing axially therethrough. The ring 30 has a first end 32 which is slightly smaller in internal diameter than an opposite second end 33 thereof.

The passageway 31 is internally threaded inward from the first end 32 with threads 34 and likewise from the second end 33 with threads 35. Extending radially outward from the ring 30 is a tap mounting plate 38. The plate 38 extends outwardly through an arc extending approximately 40 degrees along the surface of the ring 30. The plate 38 is integrally attached to the ring 30 by molding, gluing, welding or the like to ensure a fluid-tight juncture therebetween. The plate 38 has an upper surface 39 and a pair of ports or apertures 40 and 41 passing radially from the outer surface 39 to the inner passageway 31. The apertures 40 and 41 receive the taps 22 and 23 respectively.

The foraminous or screen members 16, 17 and 18 have approximately the same diameter and are designed to stack and slidably but snugly fit within the housing 15 in the passageway 31, so as to be aligned normal to fluid flow and to the axis of the housing 30, such that any fluid flowing through the passageway 31 effectively passes through the screen members 16, 17 and 18. As is best seen in FIGS. 6, 8 and 9, each of the screen members 16, 17 and 18 include an annular ring 45, 46, 47 and a screen 48, 49 and 50 respectively. Each of the rings 45, 46 and 47 has a cylindrically shaped outer surface and comprises an inner section 52 and an outer section 53, as representatively seen in FIG. 8. The ring sections 52 and 53 mate together and capture an associated screen, such as the illustrated screen 49 in FIG. 8, therebetween. The ring sections 52 and 53 interferingly engage one another and snugly hold the screen, such as screen 49, in a stretched and secure relationship across the face of the screen member 17. Radially extending outward from each of the rings 45, 46 and 47 is a peg 53, 54 and 55 respectively. The pegs 53, 54 and 55 are slidably received in the slot 36 and properly position the screen members 16, 17 and 18 relative to one another and especially relative to the taps 22 and 23.

It is foreseen that the screens may be interchangeably used with different sized mesh screens and with other devices suitable for closely determining the air flow through the passageway, as required by the gas flow volume. Where flow is unidirectional, only the center screen plus one outside screen (on the side from which the flow originates may be utilized). A suitable mesh size for the screens 48 and 50 has been found to be in the range of a screen having a mesh between 100 and 130 openings per inch and a suitable size for screen 49 has been found to be a screen having a mesh with approximately 300 to 330 openings per inch. The screens 48, 49 and 50 are preferably constructed of a matrix of approximately equally spaced vertical and horizontal wires.

The function of the screens 48 and 50 is to improve the laminar flow characteristics of the fluid passing into screen 49 and are of a mesh sufficiently small (hydraulic diameter) to produce a laminar flow downstream of the screen and the screens 48 and 50 are spaced close enough to the screen 49 to ensure the laminar characteristics are not lost prior to the gas reaching the screen 49. The open cross-sectional areas of the screens 48 and 50 are preferably such as to be at least as large as the interior cross-sectional areas of the tube adaptors 20 and 21 such that there is relatively little resistance due to a change in the open cross-sectional area thereacross. The open space cross-sectional area of the screen 49 is smaller than that of the interior of the tube adaptors 20 and 21 so as to produce a differential pressure across the screen 49 when gas flows therethrough.

Circular slots 58 and 59 are provided in the face of each of the screen member rings 45 and 46 which respectfully face the rings 46 and 47 associated with screen members 17 and 18. Received in the slots 58 and 59 are sealing means such as the illustrated O-rings 60 and 61 respectively which extend approximately five thousands of an inch out of the respective slots 58 and 59 prior to final assembly of the head 5 and which effectively seal between the associated screen member rings 45, 46 and 47 when the flow measurement head 5 is assembled such that the O-rings 59 and 60 are compressed by the rings 45, 46 and 47 being placed snugly against one another. Also positioned in the housing ring 30 on the interior surface or face 64 thereof facing the screen member ring 45 is a circumferential slot 65 having positioned therein an O-ring 66. When the flow head 5 is assembled, the screen member ring 45 abuts against the face 64 and the O-ring 65 is compressed so as to effectively seal between the face 64 and the ring 45 to prevent gaseous flow therebetween.

The housing ring 30 also includes an interior slot 68 extending circularly around the entire passageway 31. The slot 68 receives a relatively large sealing and keeper ring 69 when the head 5 is fully assembled. The ring 69 functionally retains the screen members 16, 17, and 18 in position within the head 5 snugly against one another and the face 64 and functions to seal between the screen member ring 47 and the second tube adaptor 21.

The screens 48, 49 and 50 are effectively spaced by the rings 45, 46 and 47 so as to form a first interior chamber 72 between the screens 48 and 49 and a second interior chamber 73 between the screens 49 and 50. Located in the rings 45 and 46 are bores 75 and 76 respectively. The bores 75 and 76 are aligned so as to extend radially outward from the chambers 72 and 73 through the rings 45 and 46 and coaxially align with the apertures 40 and 41 in the housing 5 respectively, as seen in FIGS. 4, 5 and 8.

The taps 22 and 23 are essentially identical in shape and tap 23, which is best illustrated in FIGS. 7 and 8, will be described in detail herein. However, it is understood that tap 22 is essentially identical to tap 23.

Tap 23 includes an elongate body 80 having a centrally located and axially aligned bore or channel 81 passing therethrough. A first tube receiving end 83 of the body 80 includes projections 84 extending radially outward therefrom. The tube receiving end 83 receives the connecting tube 7 over the projections 84 and interferingly holds the tube 7 in sealed relationship that allows flow from the channel 81 into the interior of the tube 7. The tap 22 similarly mates and flow connects with the tube 6.

Opposite the tube receiving end 83, the body includes a second end 86 with a central portion 87 of the body located between the second end 86 and tube receiving end 83. The second end 86 is of reduced outride diameter as compared to the central portion 87. The second end 86 also includes a threaded portion 89 having threads 90 thereon adapted to be received in corresponding threads 91 in the aperture 41. A distal portion 94 of the second end 86 is of a still smaller outer diameter as compared to the threaded portion 89 and extends axially outwardly therefrom. When the tap 23 is positioned in the aperture 41, the distal portion 94 extends to near but is slightly spaced from the radially inward side of the aperture 41.

Sleeved on the distal portion 94 is a sealing sleeve 96. The sealing sleeve 96 is an elongate generally annularly-shaped structure effectively filling the space radially extending between the distal portion 94 and the interior wall of the aperture 41. The sleeve 96 is constructed of a relatively low durometer silicone rubber, preferably in the ramp of 30 to 40 durometers. The sleeve, when the head 5 is assembled, sealably abuts against a shoulder 97 formed between the tap threaded portion 89 and tap distal portion 94 and against a radially outward surface 98 on the screen member ring 46. The sleeve 96, prior to assembly, is slightly longer than the distance between the shoulder 97 and the surface 98 such that the sleeve 96 is compressed into a sealing relationship, especially around the surface 98 when the head 5 is assembled. In this manner a highly sealed conduit 100 is effectively formed between the chamber 73 in the head 5 (specifically between the screens 49 and 50) and the interior of the tube 7 for effectively conveying gases under pressure between the chamber 73 and the transducer 8 without substantial leakage to the ambient atmosphere. The tap 22 is similarly constructed so as to provide a sealed conduit between the chamber 72 and the interior of the tube 6, utilizing a similar sealing sleeve 101 as described for tap 23.

A sealing O-ring 102 is also positioned between the tap central portion 87 and the housing plate 38 to seal therebetween. It is foreseen that the taps 22 and 23 may be secured to the housing 15 by means other than the disclosed threads, such as glue or the like.

The first tube adaptor 20 comprises an annular hose receiving structure 105 mounted on a disc 106 having a threaded portion 107 opposite the obstruction 105. A central passageway 108 passes entirely through the adaptor 20.

The hose receiving structure 105 is sized and shaped to receive a conventional gas transfer hose (not shown) as used in respiratory testing. The hose fits over and is secured to the outer surface of the structure 105. The disc 106 extends radially outward from the structure 105 and abuts against the housing 15 when assembled. The threaded portion 107 has threads 10 thereon designed to mate with the threads 32 on the housing. Located at the distal end of the threaded portion 107 is a knife edge 113. The knife edge 113 is formed by the end of the tube adaptor threaded portion 107 being angled at approximately 45 degrees with respect to the radius of the tube adaptor 20, thereby forming a relatively sharp and circular edge along the radially outward surface thereof. When the head 5 is assembled, the knife edge 113 is in relatively close proximity to the screen 48 normally between 0.0 and 30 thousands of an inch and is preferably approximately within two thousands of an inch of touching the screen 48 for the present embodiment so as not to apply pressure to the screen 48. The optimum placement of the edge 113 relative to the screen 48 varies with the size of the apparatus and other factors. The interior of the passageway 108 has a slightly larger diameter in the region of the threaded portion 107 as compared to the hose receiving structure 105.

The tube adaptor 21 is similar in design to the tube adaptor 20, although reversed and slightly larger on the end received by the housing 15. In particular, the tube adaptor 21 includes a hose receiving structure 116, a disc portion 117, a threaded portion 118 all interconnected and having axially passing through a central passageway 119. The hose receiving structure 116 is designed and shaped to receive a hose (not shown) of the respiratory testing type thereover for connecting to an individual, air source, analyzing machine or the like. On the axially outer surface of the threaded portion is located a set of threads 121 which mate and seal with threads 35 on the housing ring 30. The threaded portion 118 also has at a distal end thereof a knife edge 124 which is essentially a mirror image of the knife edge 113 and generally coaxially aligned therewith. The knife edge 124 is positioned to be in close proximity to the screen 50 normally between 0.0 and 30 thousands of an inch and is preferably approximately spaced two thousands of an inch therefrom for the present embodiment without applying substantial pressure to the screen 48. The housing passageways 31 is preferably coaxially aligned with the adaptor passageways 108 and 119.

It is foreseen that the head 5 of the present application can be utilized in conjunction with a conventional exterior heater.

In use, the apparatus 1 is designed to provide a measurement of the flow of fluids, especially gases through the head 5 in either direction through knowledge of the mesh and size characteristics of the screens 48, 49 and 50, screen spacing, orientation of the screens, tap spacing and the like. In particular, by measurement of the gas pressure in the chambers 72 and 73 between the screens 48, 49 and 50 a determination can be made using the pressure transducer 8 of the flow through the head 5.

During use, the knife edges 113 and 124 improve the laminar flow characteristics of the gases passing through the head 5 and subsequently improve the ability of the apparatus 1 to accurately measure the flows. The various sealing means used throughout the apparatus 1 including the O-rings 60, 61, 66 and 69 help improve the sealing characteristics between the screen members 16, 17 and 18 and consequently thereby prevent leakage around such screen members and improve the flow measuring capabilities of the apparatus 1. Further, the sealing sleeves 96 and 101 effectively seal the taps 22 and 23 relative to the rings 45 and 46 of the screen members 16 and 17 respectively so as to also prevent leakage and improve flow measuring capabilities of the apparatus 1. Finally, the integrated tap receiving plate 38 is effectively sealed with respect to the housing ring 30 so as to prevent leakage thereabout and also to improve the flow measuring accuracy of the apparatus 1.

It is to be understood that while certain forms of the present invention have been illustrated and described herein, it is not to be limited to the specific forms or arrangement of parts described and shown.

What is claimed and desired to be secured by Letters Patent is as follows:

1. In a pneumotach apparatus for measuring flows of gases and including a head having a flow passageway therethrough with a pair of hose receiving tube adaptors extending outwardly from opposite ends thereof and a plurality of flow measuring foraminous members positioned so as to extend across the passageway, the improving comprising wherein:
   (a) each of said tube adaptors has a passageway passing therethrough; each of said passageways having an inner end and an outer end;
   (b) both of said tube adaptor passageway inner ends terminating in a circular knife edge surrounding both of said passageway and the gas when passing through said passageway;
   (c) each of said passageway inner ends being in a plane positioned so as to be parallel to and less than 30 thousands of an inch from a respective one of said foraminous members, so as to reduce gaseous turbulence at said foraminous members.

2. The apparatus according to claim 1 wherein:
   (a) each of said tube adaptors respective inner ends is positioned within 0 to 2 thousands of an inch from a respective foraminous member on opposite sides of said head.

3. In a pneumotach apparatus having a flow head with at least one foraminous member extending across a passageway through said head wherein said foraminous member has an outer annular ring with a bore passing radially therethrough and said head having an aperture receiving a tap and extending from outside said head to said bore, the improvement comprising:
   (a) sealing means between a lower planar surface of said tap and an outer curved surface of said bore; said bore curved surface having a radius of curvature aligned perpendicular to said lower planar surface; said sealing means comprising an elongate sealing sleeve slidably mounted on said tap at a first end of said sleeve such that said sleeve snugly seals about said tap; said sleeve being constructed of a flexible and rubbery material; said sleeve having a second end flexibly engaging said outer curved surface of said annular ring so as to be aligned generally axially with respect to a radius of said curved surface and to seal about said bore whereby said sleeve snugly seals about both said curved outer surface and said planar surface.

4. The apparatus according to claim 3 wherein:
   (a) said sleeve having a elongate annular shape and being constructed of a relatively low durometer silicone rubber such that, when said head is assembled, said sleeve compresses and forms a sealed channel between said tap and said bore to substantially prevent leakage therefrom.

5. In a pneumotach apparatus comprising a flow head having a housing with a passageway passing through said housing and a plurality of foraminous members mounted in said passageway and including at least a pair of outer annular rings; the improvement comprising:
   (a) sealing means extending between said pair of said rings and directly engaging both of said pair of rings entirely around facing surfaces associated with each of said rings to prevent leakage of gases therebetween.

6. The apparatus according to claim 5 wherein:
   (a) said sealing means comprises a slot in a face of at least one of said annular rings; said slot receiving therein an O-ring sized to be compressed when said head is assembled.

7. A pneumotach apparatus comprising:
   (a) a generally annular housing having a first passageway therethrough;
   (b) at least two screen members mounted within said first passageway such that gaseous flow through said first passageway passes through said screen members; each of said screen members including a screen attached to an outer annular ring and forming at least one chamber therebetween; a first of said annular rings including a radially extending bore therethrough communicating directly with said chamber;
   (c) said hosing including a tap mounting plate integrally mounted on said housing so as to prevent leakage therebetween; said tap mounting plate including a tap mounted in an aperture passing through said housing; said tap being aligned to be generally coaxial with said bore; said tap having a generally planar first end in close proximity to said bore; a sealing sleeve sleeved on said tap end; said sealing sleeve being axially elongate and generally annular in shape and being constructed of a relatively low durometer material; said sleeve having a first end sealably engaging said tap planar first end; said first annular ring having an exterior curved surface with a radius of curvature perpendicular to said planar surface; said sleeve being rubbery and flexible such that upon placement of said tap into said housing said sealing sleeve is depressed and seals between both said tap and said curved surface of said annular ring having said bore therein and so as to form a sealed flow channel therebetween and to allow flow of gases between said bore and said channel without leakage therefrom;

(d) at least one of said screen member rings having a face facing at least one of the housing or a second of said screen member rings; said face having a circular slot therein; an O-ring positioned in said slot and being sized such that when said apparatus is assembled, said O-ring extends between and engages both said first ring and either said second annular ring or said housing; and (e) first and second tube adaptors; said first and second tube adaptors being sealably secured to said housing on opposite sides of said housing; said first and second tube adaptors having second and third passageways therethrough respectively that are aligned with said first passageway each having an inner end terminating with 30 thousands of an inch of respective opposed screen members; each of said first and second passageways inner ends terminating in a respective knife edge spaced in close proximity to a respective one of said screen members and being generally coaxial and mirror images of each other.

* * * * *